United States Patent
Sasaki et al.

(10) Patent No.: US 7,803,616 B2
(45) Date of Patent: Sep. 28, 2010

(54) MEDIUM SUPPLEMENT AND ANIMAL CELL CULTURE MEDIUM

(75) Inventors: Masahiro Sasaki, Fukui (JP); Hideyuki Yamada, Fukui (JP); Katsue Osada, Fukui (JP); Satoshi Terada, Fukui (JP)

(73) Assignee: Seiren Kabushiki Kaisha, Fukui-Ken (JP)

( * ) Notice: Subject to any disclaimer, the term of this patent is extended or adjusted under 35 U.S.C. 154(b) by 323 days.

(21) Appl. No.: 11/523,343

(22) Filed: Sep. 19, 2006

(65) Prior Publication Data

US 2007/0020760 A1    Jan. 25, 2007

Related U.S. Application Data

(62) Division of application No. 10/311,406, filed as application No. PCT/JP02/03836 on Apr. 17, 2002, now Pat. No. 7,157,273.

(30) Foreign Application Priority Data

Apr. 17, 2001  (JP) .............................. 2001-118559

(51) Int. Cl.
  *C12N 5/02*  (2006.01)
  *C12P 21/04*  (2006.01)
(52) U.S. Cl. ...................... 435/325; 435/70.1
(58) Field of Classification Search ............... 435/325, 435/70.1
See application file for complete search history.

(56) References Cited

FOREIGN PATENT DOCUMENTS

| EP | 1321473 | 6/1993 |
|----|---------|--------|
| JP | 1120283 A | 5/1989 |
| JP | 11-243948 | 9/1999 |
| JP | 11243948 | 9/1999 |
| WO | 0234885 | 5/2002 |

OTHER PUBLICATIONS

Patent Abstracts of Japan of JP 11-243948 dated Sep. 14, 1999.
Garel, A., et al. "Structure and Organization of the Bombyx mori Sericin 1 Gene and of the Sericins 1 Deduced from the Sequence of the Ser 1B cDNA." Insect Biochem. Molec. Biol. (1997) vol. 27, No. 5, pp. 469-477.
Minoura, N., et al. "Attachment and growth of cultured fibroblast cells on silk protein matrices." Journal of Biomedical Materials Research (1995) vol. 29, pp. 1215-1221.
English Abstract of 1 1243948 Filed Sep. 14, 1999.
English Abstract of 1120283 A Filed May 12, 1989.
Gerel A. et al., "Structure and Organization . . . cDNA", Insect Biochem. Molec. Biol., 1977, vol. 27, No. 5, pp. 469-477.
Okamoto H, et al., Structural Analysis of Sericin Genes. J. Biol. Chem., 1982, vol. 257, No. 24, pp. 15192 to 15199.
Norihisa Kato et al., "Shinki Bio Sozai Toshite No Kinu Tanpakushitsu Sericin", Bio Industry, Apr. 1998, vol. 15, No. 4, pp. 15 to 20.
Minoura, Norihiko, et al. "Attachment and Growth of Cultured Fibroblast Cells on Silk Protein Matrices" Journal of Biomedical Materials Research (1995) vol. 29, No. 10 pp. 1215-1221.
Terada, Satoshi, et al. "Sericin, A Protein Derived From Silkworms, Accelerates the Proliferation of Several Mammalian Cell Lines Including a Hybridoma" Cytotechnology, Kluwer Academic Publishers 2003 vol. 40 No. 1-3 3-12.
Webster's II New Riverside Dictionary (1984) (Houghton-Mifflin: Boston) p. 738.
Stahl et al. In Encyclopedia of Bioprocess Technology-Fermemntation, Biocatalysis, and Bioseparations. (1999) vol. 1-5. Ed.: Flinkinger (John Wiley & Sons: NY)p. 49-62.
Minoura et al. "Attachment and Growth of Cultured Fibroblast Cells on Silk Protein Matrices" J. Biomed. Mater. Res. (1995) 29: 1215-21.
Tsujimoto et al. "Cryoprotective Effect of the Serine-Rich Repetitive Sequence in Silk Protein Sericin" J. Biochem (2001) vol. 129, No. 6, pp. 979-986.

*Primary Examiner*—Sandra Saucier
*Assistant Examiner*—Susan Hanley
(74) *Attorney, Agent, or Firm*—Ladas & Parry LLP

(57) ABSTRACT

An object of the present invention is to provide a medium supplement for animal cell culture and an animal cell culture medium. The present invention relates to a medium supplement for animal cell culture comprising sericin or a sericin derivative and an animal cell culture medium comprising at least said medium supplement and a basal medium composition.

2 Claims, No Drawings

MEDIUM SUPPLEMENT AND ANIMAL CELL CULTURE MEDIUM

This application is a divisional of copending application Ser. No. 10/311,406 filed on Dec. 17, 2002 now U.S. Pat. No. 7,157,273 Granted Jan. 2, 2007, which is a 371 of PCT/JP02/03836 filed Apr. 17, 2002 is incorporated herein by reference.

BACKGROUND OF THE INVENTION

1. Field of the Invention

The present invention relates to a medium supplement for animal cell culture and an animal cell culture medium containing the same.

2. Background Art

In the field of life science, it has recently become important to produce useful substances in an industrial scale by mass culture of animal cells that produce a substance of interest, using cell culture technology or tissue culture technology. Animal cells of interest are cultured in this way with a culture medium which contains a basal medium which comprises amino acids, vitamins, inorganic salts, sugars and the like and an animal cell growth factor. As an animal cell growth factor, a serum component, such as bovine fetal serum and bovine calf serum, is generally used. Bovine fetal serum or bovine calf serum is in general needed to add to the basal medium at a level of about 5-20% by volume.

However, the serum component such as bovine fetal serum and bovine calf serum is limited in its supply and generally expensive. This will increase manufacturing cost of a product of interest. Also, serum tends to be different in its characteristics between lots, which is not desirable for culture that requires reproducibility. Further, it is sometimes difficult to purify a product from a culture supernatant of a culture medium containing the serum. Furthermore, safety of the product of interest may not be sufficiently guaranteed since there is a possibility that serum derived from animals may be infected with prions associated with mad cow disease, which is feared to cause Creutzfeldt-Jacob disease, and scrapie in sheep, as well as viruses.

Furthermore, when a medium containing serum is used in an experiment in the field of life science, the experimental system tends to become complicated, which may result in problematic confusion upon discussion of a causal relationship between cause and effect. This is because since serum comprises an extremely large variety of components including unknowns.

Therefore, attention has been drawn to cell culture media that contain known cell growth factors, hormones or the like instead of serum such as bovine fetal serum and bovine calf serum.

However, these cell growth factors or hormones are generally even more expensive than bovine fetal serum and bovine calf serum because their presence in nature is scarce, which limits their use.

Accordingly, there is a need for safe and relatively inexpensive cell growth factors or cell growth means, which can replace the abovementioned serum, known cell growth factors and the like.

In general, animal culture cells are classified into adhesive cells and suspension cells depending on their state in culture. Discussion has been made on stimulation of cell growth in animal cell mass culture by contriving appropriate means that suit to the state of cells in culture. For example, for adhesive cell culture, an attempt has been made to stimulate the cell growth by increasing adhesivity of the cells. Here, in order to increase the cell adhesivity, use of thin coating with collagen on the surface of a material of a cell culture bed has been discussed. However, the abovementioned risk of mad cow disease infection has to be contemplated since collagen is generally derived from cow, though it is relatively readily available.

Instead of the collagen-film coating treatment, use of a cell culture bed comprising silk film is suggested in Japanese Patent Laid-Open No. 11(1999)-243948 and Japanese Patent Laid-Open No. 11(1999)-253155. Such a culture bed can increase cell adhesivity and stimulate cell growth like the abovementioned collagen-coated bed; however, handling becomes complicated since a crystallization process is required to make silk protein insoluble upon film formation.

Thus, use of silk-derived components for a culture bed has been known, but use of components derived from cocoons, raw silk or the like for cell culture has not been discussed as far as the present inventors are aware.

SUMMARY OF THE INVENTION

The present inventors have now found that animal cells of interest can efficiently grow when the animal cells are cultured in a basal medium for animal cell culture supplemented with sericin which can be prepared from silkworm cocoons or the like. Further, such growth stimulating effect on animal cells by sericin has been similarly observed with chemically synthesized sericin and sericin obtained by a gene engineering method. The present invention has been made based on these findings.

Accordingly, it is an object of the present invention to provide a medium supplement for animal cell culture, which can render the excellent cell growth stimulating ability to a medium and is excellent in terms of safety and handling, and a medium for animal cell culture.

The medium supplement for animal cell culture according to the present invention comprises sericin or a sericin derivative.

Furthermore, the medium for animal cell culture according to the present invention comprises at least the abovementioned medium supplement and a basal medium composition.

According to another embodiment of the present invention, there is provided a method of culturing animal cells, which comprises the steps of adding the abovementioned medium supplement to an animal cell culture medium, culturing animal cells using the resulting medium, and growing said animal cells.

According to still another embodiment of the present invention, there is provided a method of producing a protein of interest, which comprises the steps of adding the abovementioned medium supplement to an animal cell culture medium, culturing animal cells capable of producing the protein using the resulting medium, and recovering the produced protein from said medium and/or said animal cells.

According to yet still another embodiment of the present invention, there is provided a method of replicating a virus vector of interest, which comprises the steps of adding the abovementioned medium supplement to an animal cell culture medium, culturing animal cells infected with the virus vector using the resulting medium for growth, and recovering the virus vectors from said medium and/or said animal cells.

According to another embodiment of the present invention, there is provided use of sericin or a sericin derivative for producing an animal cell growth stimulating agent.

The medium supplement according to the present invention and the medium containing the same can stimulate the growth of animal cells to be cultured and improve viability of the cells. Further, the production of a useful substance can be promoted by applying them in culturing animal cells capable of producing the useful substance of interest. Furthermore, such effects by the use of the medium supplement according to the present invention and the medium containing the same can be rendered independently of the state of the cells, i.e., suspension cells or adhesive cells, and the type of the cells, i.e., cell lines or normal cells.

Further, according to the present invention, safety of culture products can be enhanced since the amount of a serum component such as bovine fetal serum and bovine calf serum can be reduced or its use can be eliminated in culturing animal cells. The medium supplement according to the present invention is advantageous in terms of preparation and handling since cell growth can be stimulated simply by adding it to a medium. Further, sericin used in the present invention can reduce costs for production of animal cells and useful substances since it is less expensive than serum components.

DETAILED DESCRIPTION OF THE INVENTION

Medium Supplement

A medium supplement for culturing animal cells according to the present invention comprises sericin or a sericin derivative. According to a preferred embodiment of the present invention, the medium supplement is used as an animal cell growth stimulating agent.

Sericin or Sericin Derivative

Sericin or a sericin derivative in the present invention can be either naturally derived or artificially synthesized using ordinary chemical and/or genetic engineering methods, and either of them can be included.

Sericin

Sericin in the present invention implies any sericin protein all or a part of which is known to be naturally derived or synthesized. This sericin has cell growth stimulating activity.

In the present invention, naturally derived sericin is preferably obtained by a method described hereinafter.

In general, several kinds of sericin genes of 2.6 kbp to 10.6 kbp in length are confirmed and described, for example, in The Journal of Biological Chemistry 257, 15192-15199 (1982). According to one preferred embodiment of the present invention, sericin has such gene sequences.

According to one preferred embodiment of the present invention, the entire sequence of sericin essentially comprises the amino acid sequence of SEQ ID NO: 2. Typically, this amino acid sequence comprises an essential region consisting of 38 amino acids (SEQ ID NO: 1) and other nonessential regions. Preferably, sericin comprises a sequence of multiple repeats of the abovementioned essential region. For example, sericin comprising the amino acid sequence of SEQ ID NO: 2 contains 12 repeats of the essential region consisting of 38 amino acids (SEQ ID NO: 1).

Data for sericin base sequences encoding the amino acid sequence of SEQ ID NO: 2 are registered at the EMBL data library with an accession number: Z48802 and can be searched and available from NCBI home page (ncbi.nlm.nih.gov) or the like.

In this specification, the expression that "sericin essentially comprises the amino acid sequence represented by SEQ ID NO: 2" means that one or more (preferably 1 to 2000, more preferably 1 to 500, and still more preferably 1 to 300) of amino acid residues in the amino acid sequence (SEQ ID NO: 2) can be deleted, substituted, inserted or added, as long as the sericin has cell growth stimulating activity. According to a preferred embodiment, when the sericin is naturally derived, the number of amino acid residues deleted, substituted, inserted or added in the abovementioned amino acid sequence can be preferably 1 to 2000, more preferably 1 to 500, and still more preferably 1 to 300.

When the abovementioned deletions, substitutions, insertions or additions of amino acid residues are present, they are preferably located in regions other than the essential region. In this case, conservative substitutions may be placed in the essential region.

According to a more preferred embodiment of the present invention, for example, one or more, preferably 1 to 50, and more preferably 1 to 20 residues of the abovementioned amino acid sequence of sericin can be conservatively substituted as long as the sericin has cell growth stimulating activity.

The term "conservative substitution" herein means substitution of one or more amino acid residues with other chemically homologous amino acid residues substantially without changing protein activity. For example, a certain hydrophobic residue can be substituted with another hydrophobic residue, a certain polar residue can be substituted with another polar residue having the same charge, or a certain aromatic amino acid can be substituted with another aromatic amino acid. Functionally homologous amino acids which can be conservatively substituted in such a manner are known in the art for every amino acid. The following six groups are specific examples. These amino acids in the same group can be conservatively substituted with each other.

(1) Alanine (Ala), serine (Ser) and threonine (Thr)
(2) Aspartic acid (Asp) and glutamic acid (Glu)
(3) Asparagine (Asn) and glutamine (Gln)
(4) Arginine (Arg) and lysine (Lys)
(5) Isoleucine (Ile), leucine (Leu), methionine (Met), and valine (Val), and
(6) Phenylalanine (Phe), tyrosine (Tyr), and tryptophan (Trp).

In this specification, sericin naturally implies unhydrolyzed sericin (herein occasionally referred to as "sericin unhydrolysate") but also implies sericin hydrolysate. Here this sericin hydrolysate can be obtained by an ordinary method, for example, by hydrolyzing sericin using acid, alkali, enzyme or the like.

Sericin Derivative

In the present invention, a sericin derivative is a polypeptide comprising at least the amino acid sequence of SEQ ID NO: 1 consisting of 38 amino acids as an essential region. Preferably, this sericin derivative comprises the abovementioned essential region and a nonessential region(s) at its one or both ends and has cell growth stimulating ability.

The expression "having cell growth stimulating ability" herein means that cell growth stimulating activity of a polypeptide is recognized by the skilled in the art. For example, it means such a case that cell growth stimulating activity is recognized when measured under the same conditions as described in Evaluation test 1 in Example hereinafter.

Thus, the sericin derivative of the present invention may comprise an essential region only or may comprise at least the essential region and any nonessential region other than the essential region, as long as said sericin derivative has cell growth stimulating ability.

According to one preferred embodiment of the present invention, the sericin derivative has an amino acid sequence having the total length of less than 2000, more preferably less than 500, and still more preferably less than 300 residues.

Further, according to a more preferred embodiment of the present invention, the number of amino acid residues in the nonessential region(s) which can be present at one or both ends of the essential region is preferably less than 1000, more preferably less than 300, and still more preferably less than 100.

According to a preferred embodiment of the present invention, the sericin derivative has a sequence of several repeats of the abovementioned amino acid sequence of SEQ ID NO: 1. Namely, the sericin derivative comprises one or more amino acid sequences of SEQ ID NO: 1 other than the essential region. It is believed that a polypeptide having such a repetitive sequence has an improved cell growth stimulating activity.

According to a more preferred embodiment of the present invention, the sericin derivative has at least one, still more preferably at least two amino acid sequences of SEQ ID NO: 1 per 100 amino acid residues in its amino acid sequence. A high ratio of the amino acid sequence of SEQ ID NO: 1 contained in the sericin derivative is preferable. Stable cell growth stimulating activity can be attained by having repetitive sequences at such a ratio, even if the number of amino acid residues in the total length of the sericin derivative is increased.

When obtained by synthesis, the sericin derivative is preferably 2 to 8 repeats, more preferably 2 to 6 repeats, and still more preferably 2 to 4 repeats of the amino acid sequence of SEQ ID NO: 1. These figures are preferable because they are advantageous in synthetic production.

In the present invention, for example, one to several, preferably 1 to 5, more preferably 1 to 3 amino acid sequences can be conservatively substituted in the essential region of the sericin derivative.

In the present invention, the sericin derivative includes a fusion protein in which, for example, a polypeptide consisting of the abovementioned amino acid sequence of SEQ ID NO: 1 and a heterologous polypeptide (for example, another functional protein) are combined.

In this specification, the sericin derivative naturally implies an unhydrolyzed sericin or sericin derivative (herein occasionally referred to as "unhydrolysate") and further implies a hydrolysate of the sericin derivative. This hydrolysate can be obtained by hydrolyzing the sericin derivative by an ordinary method, for example, using acid, alkali, enzyme or the like.

Naturally Derived Sericin or Sericin Derivative

According to one preferred embodiment of the present invention, the sericin and the sericin derivative can be derived from natural sources. Naturally derived products are advantageous because they are highly safe to the human body and relatively inexpensive. Such sericin or a sericin derivative can be used most appropriately as a medium supplement.

According to one preferred embodiment of the present invention, the sericin or the sericin derivative is extracted from cocoons or raw silk. The cocoon means silkworm cocoon and the raw silk means silk fibers from silkworm cocoons.

In the present invention, the sericin or the sericin derivative, in particular their unhydrolysate, can be obtained from cocoons or raw silk by an ordinary extracting method. More specifically, for example, it may be obtained by extraction as a highly purified single protein at a purity of greater than 90% as follows.

First, cocoons or raw silk is treated in water, preferably in hot water at about 80-100° C. to solubilize sericin contained in the cocoons or the raw silk in the water and thus an aqueous sericin solution is obtained. The aqueous sericin solution thus obtained is treated for isolation and purification, for example, using any of the following methods (1), (2) and (3) to recover the sericin unhydrolysate of interest.

(1) The pH of the aqueous sericin solution is adjusted to 3-5 with an organic acid or inorganic acid, after which an organic coagulant or inorganic coagulant is added to precipitate sericin, and after filtration and drying, solid sericin is obtained.

(2) The aqueous sericin solution and a water soluble solvent such as methanol, ethanol and dioxane are mixed to precipitate sericin, and after filtration and drying, solid sericin is obtained.

(3) As described in Japanese Patent Laid-Open No. 04(1992)-202435, the aqueous sericin solution is applied to an ultrafiltration membrane or a reverse osmosis membrane, then specified filtration treatment is carried out, and after drying, a sericin powder is obtained.

Further in the present invention, the hydrolysate of the sericin or the sericin derivative can be obtained from cocoons or raw silk by an ordinary extraction method. More specifically, for example, it may be obtained by extraction as a highly purified single protein at a purity of greater than 90% as follows.

First, cocoons or raw silk is treated in water, preferably in hot water at about 80-100° C. to solubilize sericin contained in the cocoons or raw silk in the water and thus an aqueous sericin solution is obtained. At this stage, if necessary, sericin can be partly hydrolyzed using electrolyzed water, acid, alkali or enzyme in combination. The aqueous sericin solution thus obtained is treated for isolation and purification, for example, using the abovementioned method (1), (2) or (3) to recover the sericin hydrolysate of interest.

In the present invention, preferably, the naturally derived sericin or sericin derivative has a molecular weight distribution of 500-500,000 and contains serine at a level of 20-40% by mol as an amino acid.

Sericin or Sericin Derivative Obtained by Chemical or Genetic Engineering Method According to one preferred embodiment of the present invention, sericin and a sericin derivative can be artificially synthesized using an ordinary chemical or genetic engineering method. Typically, cell growth stimulating ability of such sericin or a sericin derivative is equal to or higher than naturally derived one. Accordingly, such sericin or a sericin derivative can also be suitably used as a medium supplement. Such chemical and genetic engineering methods for synthesis can be appropriately used in combination, if necessary.

In the present invention, the sericin and the sericin derivative can be a sequence which is all chemically synthesized or they can be obtained by using a partial sequence of a naturally derived sericin and further synthesizing based on the partial sequence. For chemical synthesis, an ordinary peptide synthesizing method such as a solid phase-liquid phase synthesis method using t-Boc method or Fmoc method can be appropriately used.

In the present invention, the sericin and the sericin derivative can be produced by a genetic engineering method. Therefore, in the present invention, when a DNA encoding the sericin or the sericin derivative is available or can be constructed, the sericin and the sericin derivative can be produced in transformed cells obtained by transforming host cells with such a DNA.

The DNA encoding a sericin-derived peptide can be obtained, for example, by cloning from the silkworm silk gland, by chemical synthesis, or by using a partial DNA obtained from the silkworm silk gland and further synthesizing based on this partial DNA. Given an amino acid sequence of a peptide, a base sequence encoding, it can be in general easily determined referring to the so-called codon table.

Accordingly, the DNAs encoding the sericin and the sericin derivative imply all the base sequences having any degenerative codons.

The sericin and the sericin derivative can be each produced by obtaining a DNA, in particular in a form of a recombinant vector, which carries a DNA fragment encoding the sericin or the sericin derivative in an expressible state and is replicable in a host cell, transforming the host cell using the DNA or the vector and culturing the transformant thus obtained. Namely, the so-called host-vector system can be used for the production of said peptide. In applying such a host-vector system, various methods for constructing expression vectors (recombinant vectors) and transformation methods commonly used in the art can be used.

Vectors used for the production of the sericin and the sericin derivative can be selected from conventional vectors for which the host-vector system has been established, such as plasmids, viruses, phages, and cosmid vectors, taking the kind of the host cell to be used into consideration. More specifically, for example, pBR, puC or pQE plasmids or lambda-phage bacteriophage is used when *Escherichia coli* is used as a host cell, pUB plasmids can be used for *Bacillus subtilis*, and YEp and YCp vectors can be used for yeasts. Plasmids are preferably used as a vector for producing said peptide.

A usable plasmid preferably contains a selective marker to select transformants. For example, a drug resistance marker, such as the ampicillin resistance and kanamycin resistance markers, or a marker gene for auxotrophy can be used as such a selective marker. Further, recovery of β-galactosidase activity by a specific peptide, which is produced by a vector DNA such as a plasmid, and a peptide encoded in a host cell can also be used as a selective marker.

Further, the DNA as a recombinant vector preferably has DNA sequences necessary to express the sericin or the sericin derivative, for example, a promoter, transcription regulatory signals such as a transcription initiation signal, translation stop signal and transcription termination signal, and translation regulatory signal.

Any cells can be used as a host cell for the production of the sericin and the sericin derivative as long as the host-vector system has been established. Examples of such a host cell include *Escherichia coli, Bacillus subtilis*, yeasts and fungi.

When *Bacillus subtilis*, yeast or fungus is used as a host cell, a secretion type vector can be used as a vector to extracellularly excrete the sericin or the sericin derivative of interest.

Further, in the present invention, the sericin derivative can be in the form of a fusion protein. Such a fusion protein is produced by constructing a DNA encoding the fusion protein by combining a DNA encoding a polypeptide comprising the abovementioned essential region and a DNA encoding a heterologous polypeptide and then expressing the DNA thus constructed.

In this specification, the terms "DNA" and "gene" are occasionally used interchangeably.

Medium for Culturing Animal Cells

An animal cell culture medium according to the present invention comprises at least the abovementioned medium supplement for animal cell culture medium and a basal medium composition. Accordingly, if necessary, it can contain various cell growth factors, for example, binding proteins such as albumin and transferrin, hormones such as insulin, epithelial growth factor (EGF), fibroid cell growth factor and various steroid hormones, and cell adhesive factors such as fibronectin, as well as serum, as long as the abovementioned components are included.

According to a preferred embodiment of the present invention, the animal cell culture medium is preferably a medium which contains serum in a smaller amount than ordinary media, and more preferably a serum-free medium. The serum-free medium is a medium which contains no serum and may contain cell growth factors and hormones other than serum.

The amount of the sericin or the sericin derivative contained in the animal cell culture medium is not particularly limited, and can be appropriately changed depending on the kind of cells to be cultured, the purpose of the culture, the kind of the basal medium composition and the like.

According to a preferred embodiment of the present invention, the percentage of the sericin or the sericin derivative in the medium is 0.001-10% by weight, more preferably 0.02-0.5% by weight, and still more preferably 0.05-0.2% by weight.

The present invention exhibits a sufficient effect even when a small amount of the sericin or the sericin derivative is contained in the medium of the present invention. However, even if they are added in a large amount, there would be generally no substantial problem since sericin is nontoxic and highly water soluble.

When the medium supplement according to the present invention is advantageously used by adding it to an ordinary medium, it is desirable to dissolve the medium supplement in a small volume of the medium and then add it to the whole medium.

In the present invention, the basal medium composition comprises carbon sources assimilatable by general animal cells, digestible nitrogen sources and inorganic salts. More specifically, for example, inorganic salts, aminoacids, glucose, and vitamins are included. If necessary, a trace substance for nutritional stimulation and an effective trace substance such as a precursor can be included in the basal medium composition.

Any medium composition known to the skilled in the art can be used as such a basal medium composition. More specifically, for example, MEM medium (H. Eagle, *Science*, 130, 432 (1959)), DMEM medium (R. Dulbecco, *Virology*, 8, 396 (1959)), RPMI 1640 medium (G. E. Moore, *J.A.M.A.*, 199, 519 (1967)), Ham's F12 medium (R. G. Ham, *Proc. Natl. Acad. Sci. U.S.A.*, 53, 288 (1965)), MCDB104 medium (W. L. Mckeehan, In Vitro, 13, 399 (1977)), and MCDB153 medium (D. M. Peehe, In Vitro, 16, 526 (1980)) can be used.

Other media which can be appropriately used in the present invention include serum-free medium ASF104 (Ajinomoto Co., Inc.), serum-free medium SF-02 (Sanko Junyaku Co., Ltd.), serum-free medium Hybridoma-SFM (Lifetech Oriental), serum-free medium BIO-MPM-1 (Biological Industries), serum-free medium EX-CELL™ 302-HDP (JRH Biosciences), serum-free medium Cosmedium 001 (Cosmo Bio), and serum-free medium SFM-101 (Nissui Pharmaceutical Co., Ltd.).

Animal cells which can be cultured in a medium of the present invention are not particularly limited and they can be either established cell lines or nonestablished normal cells obtained from biological tissues. Accordingly, animal cells of the present invention can be, for example, cells which can produce proteins by themselves, cells which are transformed by genetic engineering to express heterologous proteins, or cells which are infected with various virus vectors.

Examples of the cells which can produce proteins by themselves include hybridoma cells producing monoclonal antibodies, leucocytes producing interferon (IFN)-α, fibroblasts producing IFN-β, lymphocytes producing IFN-γ, human kidney cells producing prourokinase (pro-UK) or UK, melanoma cells producing tissue plasminogen activator (tPA), In-111 cells producing insulin, HIT cells producing glucagon, HepG2 cells producing erythropoietin, and B151K12 cells producing interleukin-5.

Examples of the cell lines transformed by genetic engineering include Vero cells, HeLa cells, CHO (Chinese hamster ovary) cells, HKG cells, NIH3T3 cells, BHK cells, COS-1 cells, COS-7 cells, and myeloma cells.

Examples of the cells infected with virus vectors include those infected with retrovirus vectors, lentivirus vectors, adenovirus vectors, adeno-associated virus vectors, and herpesvirus vectors. These virus vectors can be genetically recombined by an ordinary genetic engineering method. Further, examples of the animal cells which are infected with these virus vectors and cultured using the medium of the present invention include HEK (human embryonic kidney) 293 cells, A549 cells, and PER.C6 cells.

Another preferred embodiment of the present invention provides a method of culturing animal cells, which comprises the steps of adding the medium supplement of the present invention to an animal cell culture medium and culturing animal cells using the resulting medium to grow the animal cells.

Culture conditions for this method, for example, the oxygen concentration, osmotic pressure, pH, temperature of the medium, can be appropriately changed depending on the kind of the cells to be cultured, the purpose of the culture, the volume of the culture, and the kind of the basal medium composition. Any culture system such as batch culture, continuous culture or perfusion culture can be used. High density culture can also be used.

Still another preferred embodiment of the present invention provides a method of producing a protein, comprising the steps of adding the medium supplement of the present invention to an animal cell culture medium, culturing animal cells capable of producing the protein using the resulting medium to grow the animal cells, and recovering the produced protein from said medium and/or said animal cells.

In the method of producing a protein according to the present invention, examples of the protein which can preferably be produced include monoclonal antibodies, IFN-α, IFN-β, INF-γ, pro-UK or UK, tPA, insulin, glucagon, erythropoietin, and interleukin-5.

The protein produced can be recovered using chemical or physical characteristics of the protein and isolated and purified by various ordinary isolation methods. For example, the protein can be recovered, isolated and purified by treatment with a protein coagulant, ultrafiltration, absorption chromatography, ion-exchange chromatography, affinity chromatography, molecular sieving chromatography, dialysis or the like, singly or in combination.

Another embodiment of the present invention provides a method of replicating a virus vector, which comprises the steps of adding the medium supplement of the present invention to an animal cell culture medium, culturing to grow animal cells infected with the virus vectors using the resulting medium and recovering the produced virus vectors from said medium and/or said animal cells.

Virus vectors replicable by the method of replication of the present invention are various virus vectors described above as examples and can be created by genetic recombination, if necessary.

Appropriately selected animal cells are infected with the virus vectors of interest by an ordinary method.

Further, the virus vectors can be recovered from grown cells by isolation and purification using various ordinary isolation methods such as ultrafiltration and centrifugation. Here it is desirable to appropriately select the method of recovering virus vectors according to the kind of virus vectors.

Generally, gene therapies are categorized into two kinds, i.e., ex vivo gene therapy and in vivo gene therapy. The former is a therapeutic method in which cells derived from a patient are first cultured outside the body and then treated for gene transfer, after which the cells are administered to the patient. The latter is a therapeutic method in which vectors with transferred genes are directly introduced into the patient's body.

The method according to the present invention can replicate virus vectors, into which genes used for such gene therapies are introduced, more efficiently than conventional methods. Further, the medium of the present invention exhibits excellent growth stimulating effect on the animal cells used for such a replication method, such as 293 cells.

EXAMPLES

The present invention is further illustrated by the following examples that are not intended as a limitation of the invention.

Methods for producing sericin or a sericin derivative are shown in the following Production Example 1 and Production Example 2.

Production Example 1

One kilogram of cocoons (made by silkworms (*Bombyx mori*)) was treated in 50 L of 0.2% sodium carbonate solution (pH 11-12) at 95° C. for 2 hours to extract sericin hydrolysate. The resulting sericin hydrolysate extract was filtered using a filter having an average pore diameter of 0.2 μm to remove precipitate, after which the filtrate was desalted using a reverse osmosis membrane to obtain a transparent and colorless aqueous solution of the sericin hydrolysate having a sericin concentration of 0.2%.

This aqueous solution was concentrated using an evaporator to a sericin concentration of about 2%, and then lyophilized to obtain 100 g of powdery sericin hydrolysate (polypeptide A) having an average molecular weight of 20,000 at a purity of greater than 90%.

Production Example 2

Chemical Synthesis of DNA Fragment Encoding Sericin Derivative:

A DNA was designed to encode a polypeptide, as one example of the sericin derivative, comprising the following amino acid sequence including two repeats of the sequence (SEQ ID NO: 1) consisting of 38 amino acids which is commonly conserved in sericin:

```
Ser-Ser-Thr-Gly-Ser-Ser-Ser-Asn-Thr-    (SEQ ID NO: 4)
Asp-Ser-Asn-Ser-Asn-Ser-Ala-Gly-Ser-
Ser-Thr-Ser-Gly-Gly-Ser-Ser-Thr-Tyr-
Gly-Tyr-Ser-Ser-Asn-Ser-Arg-Asp-Gly-
Ser-Val-Ser-Ser-Thr-Gly-Ser-Ser-Ser-
Asn-Thr-Asp-Ser-Asn-Ser-Asn-Ser-Ala-
Gly-Ser-Ser-Thr-Ser-Gly-Gly-Ser-Ser-
Thr-Tyr-Gly-Tyr-Ser-Ser-Asn-Ser-Arg-
Asp-Gly-Ser-Val.
```

Here the recognition site (Ile-Glu-Gly-Arg (SEQ ID NO: 5)) of protease (Factor Xa) was placed at the N terminus of the abovementioned peptide to cleave another fused peptide. Further, restriction enzyme recognition sites (PstI, EcoRI) were placed at both termini of the DNA encoding the abovementioned peptide to bind to a vector and two translation stop codons were added to the 3' terminal side of the DNA. In this way, the DNA encoding the abovementioned polypeptide was designed.

Next, the designed DNA was chemically synthesized using a DNA synthesizer (Applied Biosystems) by the phosphoamidite method. Specifically, eight fragments each having a DNA length of about 60-70 bases were chemically synthesized.

The synthesized eight DNA fragments were as follows:

```
Fragment (1):
5'-GTGATCAATCGAAGGTCGCTCGAGTACTGGT   (SEQ ID NO: 6)
TCTTCTTCTAACACCGACTCTAACTCTAAC-3'

Fragment (2):
5'-TCTGCTGGTTCTTCTACCTCTGGTGGTTCTT   (SEQ ID NO: 7)
CTACCTACGGTTACTCTTCTAACTCTCGTGACGG
TTCT-3'

Fragment (3):
5'-GTTTCTTCTACCGGTTCTTCTTCTAACACCG   (SEQ ID NO: 8)
ACTCTAACTCTAACTCTGCTGGTTCTTCTACCT
C-3'

Fragment (4):
5'-TGGTGGTTCTTCTACCTACGGTTACTCTTCT   (SEQ ID NO: 9)
AACTCTCGTGACGGATCCGTTTAATAGCTGAGC
G-3'

Fragment (1'):
5'-CAGAGTTAGAGTTAGAGTCGGTGTTAGAAGA   (SEQ ID NO: 10)
AGAACCAGTACTCGAGCGACCTTCGATTGATCAC
TGCA-3'

Fragment (2'):
5'-AAACAGAACCGTCACGAGAGTTAGAAGAGTA   (SEQ ID NO: 11)
ACCGTAGGTAGAAGAACCACCAGAGGTAGAAGAA
CCAG-3'

Fragment (3'):
5'-ACCAGAGGTAGAAGAACCAGCAGAGTTAGAG   (SEQ ID NO: 12)
TTAGAGTCGGTGTTAGAAGAAGAACCGGTAGAA
G-3'

Fragment (4'):
5'-AATTCGCTCAGCTATTAAACGGATCCGTCAC   (SEQ ID NO: 13)
GAGAGTTAGAAGAGTAACCGTAGGTAGAAGAAC
C-3'
```

Construction of DNA Encoding Peptide

The eight fragments (about 70 bases) synthesized as described above were converted into double-stranded chains by annealing with fragments each having a complementary sequence to obtain four double-stranded DNA fragments consisting of DNA encoding the peptide.

Further, since a chemically synthesized oligonucleotide has no phosphoric acid at the 5' terminus, phosphoric acid was added to the 5' terminus of each of the synthesized gene fragments using T4 polynucleotide kinase (Takara Shuzo Co., Ltd.).

Next, the four DNA fragments were ligated using Takara Ligation Kit Version II (Takara Shuzo Co., Ltd.).

Construction of Expression Plasmid for *Escherichia coli*:

The ligated DNA fragment was mixed with a high expression vector pQE 30 for *Escherichia coli* (Qiagen) and a ligation reaction was carried out using Takara Ligation Kit Version II (Takara Shuzo Co., Ltd.). The resulting reaction mixture was introduced into *Escherichia coli* JM109 and then an expression plasmid, into which the DNA fragment was inserted, was obtained from the transformant.

Expression Induction:

*E. coli* JM109 strain transformant cells, into which the expression plasmid carrying the recombinant gene encoding the polypeptide was introduced, were cultured in M9+2% casamino acid medium supplemented with 50 µg/ml ampicillin at 37° C. overnight with shaking. After culturing, the resulting culture was inoculated into the same medium at a concentration of 2%, and incubation was further continued at 37° C. with shaking.

IPTG (isopropyl-β-D-thiogalctopyranoside) at a final concentration of 1 mM was added to the resulting culture when the optical density at 610 nm reached 0.3-0.5, and incubation was further continued for 4 hours.

Purification of Peptide:

After the expression induction, the cells were broken by ultrasonication and the resulting suspension was treated at 100° C. for 10 minutes and centrifuged at 6,500 rpm for 5 minutes to recover the polypeptide as a soluble fraction from the supernatant.

Next, the polypeptide was purified using QIA Express Ni-NTA Protein Purification System (Qiagen).

A sericin derivative (polypeptide B) having a molecular weight of about 8,000 was thus obtained by the method described above.

Evaluation Test

The following evaluation tests were carried out using the sericin and the sericin derivatives (polypeptides A and B) obtained in the Production Examples above.

Evaluation Test 1: Stimulating Effect on Hybridoma Cell Growth and Stimulating Effect on Antibody Production Sericin or bovine serum albumin (BSA) was added to and dissolved in a serum-free basal medium ASF104 (Ajinomoto Co., Inc.) at a specified concentration to prepare each of the media for 7 different experimental groups shown in Table 1 below.

Antibody producing mouse hybridoma cells (F. Makishima, Cytotechnology, 10, 15 (1992)) were inoculated at a cell density of $1.5 \times 10^4$ (cells/ml) into each of the media for experimental groups provided in wells of a 24-well culture plate. The hybridoma cells used were suspension cells.

Cells of each experimental group were cultured at 37° C. for 3 days in an atmosphere of 5% $CO_2$ and 95% air by volume.

After culturing, cell density of the culture was measured using an ordinary hemocytometer. Cell growth stimulating effect for each experimental group was evaluated from the change in the cell density.

The amount of antibodies produced in the culture supernatant was quantitatively measured by an ordinary enzyme-linked immunosorbent assay method (ELISA method) using protein G purified antibody as a standard. In the measurement, horseradish peroxidase-labeled antimouse-IgG (G+L) was used as an enzyme-labeled secondary antibody, and o-phenylenediamine was used as a color former. The amount of antibody in the cell-free culture supernatant was expressed by the IgG concentration (µg/ml) in a medium. Antibody productivity in each experimental group was evaluated from the change in antibody concentration.

Results obtained have been shown in Table 1 below.

TABLE 1

| Experimental group | Cell density ($10^4$ cells/ml) | Antibody concentration (µg/ml) |
|---|---|---|
| No supplement added | 8.2 ± 1.5 | 19 ± 2 |
| Polypeptide A 0.05% | 16.5 ± 2.0 | 22 ± 2 |
| Polypeptide A 0.1% | 18.5 ± 1.3 | 23 ± 1 |
| BSA 0.05% | 15.5 ± 0.8 | 20 ± 1 |
| BSA 0.1% | 18.2 ± 1.7 | 18 ± 1 |
| Polypeptide A and BSA, 0.05% each | 23.4 ± 0.6 | 24 ± 2 |
| Polypeptide B 0.1% | 22.3 ± 0.6 | 23 ± 2 |

Average ± standard deviation (n = 3)

These results showed that the media according to the present invention (each medium supplemented singly with polypeptide A or polypeptide B) could strongly stimulate the growth and antibody productivity of the hybridoma cells. The effect was at least equal to or greater than with the media supplemented with BSA.

Evaluation Test 2: Stimulating Effect on HepG2 Cell Growth, Enhancing Effect on Albumin Secretion and Stimulating Effect on Survivability Polypeptide A, polypeptide B or BSA was added to and dissolved in a serum-free medium SF-02 (Sanko Junyaku Co., Ltd.) at a specified concentration to prepare each of the media for 6 different experimental groups shown in Table 2 below.

HepG2 cells derived from human liver cancer cells (J. Skelly, Nature, 282, 615 (1979)) were inoculated at a cell density of $1.0 \times 10^4$ (cells/ml) into wells of a 24-well culture plate. The HepG2 cells used were adhesive cells.

Cells of each experimental group were cultured at 37° C. in an atmosphere of 5% $CO_2$ and 95% air by volume.

After culturing, cell density of the culture was measured using an ordinary hemocytometer. Cell growth stimulating effect for each experimental group was evaluated from the change in cell density.

Cell survivability was assessed by trypane blue staining and viable cell counting.

The amount of albumin secreted was quantitatively measured by an ordinary enzyme-linked immunosorbent assay method (ELISA method) using commercial purified human serum albumin as a standard. In the measurement, horseradish peroxidase-labeled antibody was used as an enzyme-labeled antibody, and o-phenylenediamine was used as a color former.

Results obtained have been shown in Table 2 below.

TABLE 2

| Experimental group | Cell density of culture at day 5 ($10^4$ cells/ml) | Secreted albumin in culture at day 5 (ng/ml) | Survivability in culture at day 17 (%) |
|---|---|---|---|
| No supplement added | 7.9 ± 0.6 | 390 ± 23 | 3.1 ± 0.5 |
| Polypeptide A 0.05% | 13.5 ± 0.4 | 431 ± 28 | 8.6 ± 0.4 |
| Polypeptide A 0.1% | 17.3 ± 1.1 | 476 ± 19 | 10.3 ± 0.8 |
| BSA 0.05% | 12.1 ± 0.8 | 420 ± 13 | 4.9 ± 0.4 |
| BSA 0.1% | 15.5 ± 0.7 | 448 ± 24 | 6.2 ± 0.3 |
| Polypeptide A and BSA, 0.05% each | 19.4 ± 1.2 | 510 ± 21 | 12.4 ± 0.7 |
| Polypeptide B 0.1% | 20.1 ± 1.5 | 525 ± 19 | 13.0 ± 0.4 |

Average ± standard deviation (n = 3)

These results showed that the media according to the present invention strongly stimulated the growth of HepG2 cells and protein productivity characteristic to liver functions, such as albumin secretion. Generally, when cells are cultured without changing a medium, most of the cells are killed due to overgrowth. In contract, cell survivability could be increased in the media according to the present invention.

Evaluation Test 3: Growth Stimulating Effect on Human Epidermal Keratinocyte Cells Polypeptide A or B was added to and dissolved in a medium for epidermal keratinocyte cells (CCM-3111, Clonetics Corporation (California, USA)) at a specified concentration to prepare each of the media for 4 different experimental groups shown in Table 3 below.

Neonatal epidermal keratinocyte cells (Normal Human Epidermal Keratinocyte cells, Clonetics Corporation (California, USA)) were inoculated at a cell density of $1.0 \times 10^4$ (cells/ml) into wells of a 24-well culture plate. The cells used were normal cells and not cell line-derived and were adhesive cells.

Cells in each experimental group were cultured at 37° C. in an atmosphere of 5% $CO_2$ and 95% air by volume.

After culturing, cell density of the culture was measured using an ordinary hemocytometer. Stimulating effect on cell growth for each experimental group was evaluated from the change in cell density.

Results obtained have been shown in Table 3 below.

TABLE 3

| Experimental group | Cell density ($10^4$ cells/ml) |
|---|---|
| No supplement added | 3.4 ± 0.1 |
| Polypeptide A 0.01% | 5.5 ± 1.3 |
| Polypeptide A 0.05% | 5.8 ± 0.8 |
| Polypeptide B 0.01% | 5.9 ± 1.5 |
| Polypeptide B 0.05% | 6.3 ± 0.4 |

Average ± standard deviation (n = 3)

Occasionally, BSA cannot be added to a medium because cells rather differentiate than proliferate when normal cells like epidermal keratinocyte cells are cultured in a medium supplemented with BSA. The results above confirmed that the media according to the present invention stimulated the growth of epidermal keratinocyte cells and did not induce cell differentiation.

Evaluation Test 4: Stimulating Effect on Adenovirus Vector Production

This test was carried out using Takara Adenovirus Expression Vector Kit (Takara Shuzo Co., Ltd.).

$4 \times 10^7$ PFU of adenovirus was added to a medium (Nephrigen; Celox (Minnesota, USA)) containing $9.5 \times 10^5$ of 293 cells and the admixture was allowed to stand for one hour to infect the cells with the virus.

Next, the medium with cultured cells was replaced by 3 different media for experimental groups shown in Table 4 below (one medium without sericin and two media each containing 0.02% polypeptide A or polypeptide B) and incubation was further continued for 3 days for viral production. Cells of each experimental group were cultured at 37° C. in an atmosphere of 5% $CO_2$ and 95% air by volume.

After culturing, the resulting virus suspension was recovered and the virus titer was determined using 293 cells. The virus titer was calculated by a TCID 50 method (50% tissue culture influence dose).

Results obtained have been shown in Table 4 below.

TABLE 4

| Experimental group | Virus titer (×10⁷ PFU) |
| --- | --- |
| No supplement added | 3.36 ± 1.50 |
| Polypeptide A 0.02% added | 5.18 ± 1.22 |
| Polypeptide B 0.02% added | 7.62 ± 2.04 |

The results showed that the medium supplemented with sericin or a sericin derivative according to the present invention stimulated production of virus vector used for gene therapy. Such effect was highly marked with polypeptide B.

The invention claimed is:

1. A method of culturing animal cells, comprising the steps of culturing animal cells using a medium for animal cell culture to grow said animal cells, wherein the medium for animal cell culture comprises:
   a basal medium composition for animal cell culture; and
   sericin comprising at least a polypeptide consisting of the amino acid sequence of SEQ ID NO: 2 or a sericin derivative comprising at least a polypeptide consisting of the amino acid sequence of SEQ ID NO: 1 as an essential region, or at least a polypeptide consisting of a modified amino acid sequence of SEQ ID NO: 2 in which one or more amino acid residues are conservatively substituted wherein the sericin or the sericin derivative is mixed with the basal medium and wherein the growth of the animal cells is stimulated by the sericin or the sericin derivative.

2. A method of producing a protein of interest, comprising the steps of culturing animal cells capable of producing the protein of interest using a medium for animal cell culture, and recovering the produced protein from said medium and/or said animal cells, wherein the medium for animal cell culture comprises:
   a basal medium composition for animal cell culture; and
   sericin comprising at least a polypeptide consisting of the amino acid sequence of SEQ ID NO: 2 or a sericin derivative comprising at least a polypeptide consisting of the amino acid sequence of SEQ ID NO: 1 as an essential region, or at least a polypeptide consisting of a modified amino acid sequence of SEQ ID NO: 2 in which one or more amino acid residues are conservatively substituted wherein the sericin or the sericin derivative is mixed with the basal medium and wherein the growth of the animal cells is stimulated by the sericin or the sericin derivative.

* * * * *

SEQUENCE LISTING

<160> NUMBER OF SEQ ID NOS: 13

<210> SEQ ID NO 1
<211> LENGTH: 38
<212> TYPE: PRT
<213> ORGANISM: Artificial Sequence
<220> FEATURE:
<223> OTHER INFORMATION: Peptides derived from sericin

<400> SEQUENCE: 1

Ser Ser Thr Gly Ser Ser Ser Asn Thr Asp Ser Asn Ser Asn Ser Ala
1               5                   10                  15

Gly Ser Ser Thr Ser Gly Gly Ser Ser Thr Tyr Gly Tyr Ser Ser Asn
            20                  25                  30

Ser Arg Asp Gly Ser Val
        35

<210> SEQ ID NO 2
<211> LENGTH: 1217
<212> TYPE: PRT
<213> ORGANISM: Bombyx Mori

<400> SEQUENCE: 2

Met Arg Phe Val Leu Cys Cys Thr Leu Ile Ala Leu Ala Ala Leu Ser
1               5                   10                  15

Val Lys Ala Phe Gly His His Pro Gly Asn Arg Asp Thr Val Glu Val
            20                  25                  30

Lys Asn Arg Lys Tyr Asn Ala Ala Ser Ser Glu Ser Ser Tyr Leu Asn
        35                  40                  45

Lys Asp Asn Asp Ser Ile Ser Ala Gly Ala Arg Ala Lys Ser Val
    50                  55                  60

Glu Gln Ser Gln Asp Lys Ser Lys Tyr Thr Ser Gly Pro Glu Gly Val
65                  70                  75                  80

Ser Tyr Ser Gly Arg Ser Gln Asn Tyr Lys Asp Ser Lys Gln Ala Tyr
                85                  90                  95

Ala Asp Tyr His Asn Asp Pro Asn Gly Gly Ser Ala Ser Ala Gly Gln
            100                 105                 110

Ser Arg Asp Thr Ser Leu Arg Glu Arg Lys Val Asn Tyr Val Ser Asp
        115                 120                 125

Gly Gln Ala Val Ala Ala Ser Ser Asp Ala Arg Asp Glu Asn Arg Ser
    130                 135                 140

Ala Gln Gln Asn Ala Gln Ala Asn Trp Asn Ala Asp Gly Ser Tyr Gly
145                 150                 155                 160

Val Ser Ala Asp Arg Ser Gly Ser Ala Ser Ser Arg Arg Gln Ala
                165                 170                 175

Asn Tyr Tyr Ser Asp Lys Asp Ile Thr Ala Ala Ser Lys Asp Asp Ser
            180                 185                 190

-continued

```
Arg Ala Asp Ser Ser Arg Arg Ser Asn Ala Tyr Tyr Asn Arg Asp Ser
        195                 200                 205

Asp Gly Ser Glu Ser Ala Gly Leu Ser Asp Arg Ser Ala Ser Ser Ser
        210                 215                 220

Lys Asn Asp Asn Val Phe Val Tyr Arg Thr Lys Asp Ser Ile Gly Gly
225                 230                 235                 240

Gln Ala Lys Ser Arg Ser Ser His Ser Gln Glu Ser Asp Ala Tyr
                245                 250                 255

Tyr Asn Ser Ser Pro Asp Gly Ser Tyr Asn Ala Gly Thr Arg Asp Ser
                260                 265                 270

Ser Thr Ser Asn Lys Lys Lys Ala Ser Ser Thr Ile Tyr Ala Asp Lys
        275                 280                 285

Asp Gln Ile Arg Ala Ala Asn Asp Arg Ser Ser Ser Lys Gln Leu Lys
        290                 295                 300

Gln Ser Ser Ala Gln Ile Ser Ser Gly Pro Lys Gly Thr Ser Val Ser
305                 310                 315                 320

Ser Lys Asp Arg Gln Tyr Ser Asn Asp Lys Arg Ser Lys Ser Asp Ala
                325                 330                 335

Tyr Val Gly Arg Asp Gly Thr Val Ala Tyr Ser Asn Lys Asp Ser Glu
                340                 345                 350

Lys Thr Ser Arg Gln Ser Asn Thr Asn Tyr Ala Asp Gln Asn Ser Val
        355                 360                 365

Arg Ser Asp Ser Ala Ala Ser Asp Gln Thr Ser Lys Ser Tyr Asp Arg
        370                 375                 380

Gly Tyr Ser Asp Lys Asn Ile Val Ala His Ser Ser Gly Ser Arg Gly
385                 390                 395                 400

Ser Gln Asn Gln Lys Ser Ser Ser Tyr Arg Ala Asp Lys Asp Gly Phe
                405                 410                 415

Ser Ser Ser Thr Asn Thr Glu Lys Ser Lys Phe Ser Ser Ser Asn Ser
                420                 425                 430

Val Val Glu Thr Ser Asp Gly Ala Ser Ala Ser Arg Glu Ser Ser Ala
        435                 440                 445

Glu Asp Thr Lys Ser Ser Asn Ser Asn Val Gln Ser Asp Glu Thr Gly
        450                 455                 460

Glu Glu Glu Glu Leu Phe Asp Val Val Ser Tyr Gln Lys Ile Glu Asp
465                 470                 475                 480

Gly Lys Pro Val Ile Ile Met Lys Val Ile Pro Val Glu Lys Ser Ala
                485                 490                 495

Ser Gln Ser Ser Ser Arg Ser Ser Gln Glu Ser Ala Ser Tyr Ser
                500                 505                 510

Ser Ser Ser Ser Ser Thr Leu Ser Glu Asp Ser Ser Glu Val Asp
        515                 520                 525

Ile Asp Leu Gly Asn Leu Gly Trp Trp Trp Asn Ser Asp Asn Lys Ala
        530                 535                 540

Gln Arg Ala Ala Gly Gly Ala Thr Lys Ser Glu Ala Ser Ser Ser Thr
545                 550                 555                 560

Gln Ala Thr Thr Val Ser Gly Ala Asp Asp Ser Ala Asp Ser Tyr Thr
                565                 570                 575

Trp Trp Trp Asn Pro Arg Arg Ser Ser Ser Ser Ser Ser Ala Ser
                580                 585                 590

Ser Ser Ser Ser Gly Ser Asn Val Gly Gly Ser Ser Gln Ser Ser Gly
        595                 600                 605

Gln Ser Thr Ser Gly Ser Asn Ala Arg Gly His Leu Gly Thr Val Ser
```

```
                610             615             620
Ser Thr Gly Ser Thr Ser Asn Thr Asp Ser Ser Lys Ser Ala Gly
625             630             635             640

Ser Arg Thr Ser Gly Gly Thr Ser Thr Tyr Gly Tyr Ser Ser His
            645             650             655

Arg Gly Gly Ser Val Ser Ser Thr Gly Ser Ser Ser Asn Thr Asp Ser
            660             665             670

Ser Thr Lys Asn Ala Gly Ser Ser Thr Ser Gly Gly Thr Ser Thr Tyr
            675             680             685

Gly Tyr Ser Ser His Arg Gly Gly Ser Val Ser Thr Gly Ser
690             695             700

Ser Ser Asn Thr Asp Ser Ser Thr Lys Ser Ala Gly Ser Ser Thr Ser
705             710             715             720

Gly Gly Thr Ser Thr Tyr Gly Tyr Ser Ser Arg His Arg Gly Gly Ser
            725             730             735

Val Ser Ser Thr Gly Ser Ser Ser Asn Thr Asp Ser Ser Thr Lys Asn
            740             745             750

Ala Gly Ser Arg Thr Ser Gly Gly Thr Ser Thr Tyr Gly Tyr Ser Ser
            755             760             765

Ser His Arg Gly Gly Ser Val Ser Ser Thr Gly Ser Ser Ser Asn Thr
770             775             780

Asp Ser Ser Thr Lys Asn Ala Gly Ser Arg Thr Ser Gly Gly Thr Ser
785             790             795             800

Thr Tyr Gly Tyr Ser Ser His Arg Gly Gly Ser Val Ser Ser Thr
            805             810             815

Gly Ser Ser Ser Asn Thr Asp Ser Ser Thr Lys Asn Ala Gly Ser Arg
            820             825             830

Thr Ser Gly Gly Thr Ser Thr Tyr Gly Tyr Ser Ser His Arg Gly
            835             840             845

Gly Ser Val Ser Ser Thr Gly Ser Ser Ser Asn Thr Asp Ser Ser Thr
            850             855             860

Lys Asn Ala Gly Ser Ser Thr Ser Gly Gly Ser Ser Thr Tyr Gly Tyr
865             870             875             880

Ser Ser Asp Ser Arg Asp Gly Ser Val Ser Ser Thr Gly Ser Ser Ser
            885             890             895

Asn Thr Asp Ala Ser Thr Asp Leu Ala Gly Ser Ser Thr Ser Gly Gly
            900             905             910

Ser Ser Thr Tyr Gly Tyr Ser Ser Asp Ser Arg Asp Gly Ser Val Ser
            915             920             925

Ser Thr Gly Ser Ser Ser Asn Thr Asp Ala Ser Thr Asp Leu Ala Gly
930             935             940

Ser Ser Thr Ser Gly Gly Ser Ser Thr Tyr Gly Tyr Ser Ser Asp Ser
945             950             955             960

Arg Asp Gly Ser Val Ser Ser Thr Gly Ser Ser Asn Thr Asp Ala
            965             970             975

Ser Thr Asp Leu Thr Gly Ser Ser Thr Ser Gly Gly Ser Ser Thr Tyr
            980             985             990

Gly Tyr Ser Ser Asp Ser Arg Asp Gly Ser Val Ser Ser Thr Gly Ser
            995             1000            1005

Ser Ser Asn Thr Asp Ala Ser Thr Asp Leu Ala Gly Ser Ser Thr
            1010            1015            1020

Ser Gly Gly Ser Ser Thr Tyr Gly Tyr Ser Ser Asn Arg Asp
            1025            1030            1035
```

```
Gly Ser Val Ser Ala Thr Gly Ser Ser Asn Thr Asp Ala Ser
    1040                1045                1050

Thr Thr Glu Glu Ser Thr Ser Ala Gly Ser Ser Thr Glu Gly
    1055                1060                1065

Tyr Ser Ser Ser Ser His Asp Gly Ser Val Thr Ser Thr Asp Gly
    1070                1075                1080

Ser Ser Thr Ser Gly Gly Ala Ser Ser Ser Ala Ser Thr Ala
    1085                1090                1095

Lys Ser Asp Ala Ala Ser Glu Asp Gly Phe Trp Trp Trp Asn
    1100                1105                1110

Arg Arg Lys Ser Gly Ser Gly His Lys Ser Ala Thr Val Gln Ser
    1115                1120                1125

Ser Thr Thr Asp Lys Thr Ser Thr Asp Ser Ala Ser Ser Thr Asp
    1130                1135                1140

Ser Thr Ser Ser Thr Ser Gly Ala Ser Thr Thr Thr Ser Gly Ser
    1145                1150                1155

Ser Ser Thr Ser Gly Gly Ser Ser Thr Ser Asp Ala Ser Ser Thr
    1160                1165                1170

Ser Ser Ser Val Ser Arg Ser His His Ser Gly Val Asn Arg Leu
    1175                1180                1185

Leu His Lys Pro Gly Gln Gly Lys Ile Cys Leu Cys Phe Lys Asn
    1190                1195                1200

Ile Phe Asp Ile Pro Tyr His Leu Arg Lys Asn Ile Gly Val
    1205                1210                1215

<210> SEQ ID NO 3
<211> LENGTH: 3651
<212> TYPE: DNA
<213> ORGANISM: Bombyx Mori

<400> SEQUENCE: 3
atgcgtttcg ttctgtgctg cactttgatt gcgttggctg cgctcagcgt aaaagctttc    60
ggtcaccacc ccggcaatcg agatacagtc gaagtcaaaa accgaaagta caatgcagct   120
agcagtgaaa gctcttacct caacaaagat aatgattcga taagtgccgg agcgcgccgt   180
gccaagtccg tagagcagag tcaggataaa agcaaatata catctggtcc agaaggcgtg   240
tcgtacagcg gaaggtctca gaactataaa gattccaagc aagcttatgc cgattatcac   300
aacgatccga acggcggatc tgcttctgcg ggacaatctc gcgacacgag cctgagggag   360
agaaaagtaa attacgtctc tgacggtcaa gcagtggccg cttccagtga cgctcgcgat   420
gaaaaccgat ccgcccaaca gaatgctcag gccaattgga acgctgacgg ttcttacgga   480
gttagcgctg atcgaagtgg ttccgctagt tctagacgcc gccaagccaa ttactactcc   540
gataaagaca tcactgctgc ttctaaagac gattcacgtg cagattcttc taggagaagc   600
aatgcctatt acaacagaga tagtgacggc tcagaatccg ctggattaag tgaccgtagt   660
gcttcttcct cgaaaaatga taatgtattt gtttaccgca ctaaggattc tattggagga   720
caagcgaaat cttcaagatc atctcattca caagagagcg acgcttatta taactccagt   780
ccggatggaa gctacaacgc tggtacgcga gacagttcaa cttctaacaa aagaaggcg    840 agctctacca tctacgctga taaggatcaa atacgcgccg cgaatgatcg ttcttcttcg   900
aaacagttaa aacagagcag cgctcaaatc tcctccgggc aaagggcac ctctgtaagc    960 agtaaggata ggcaatactc gaacgacaaa cgcagcaaat ctgatgcgta cgtcggacgg  1020
```

```
gacggcaccg ttgcttactc aaacaaggac agcgaaaaga cctcacgaca aagtaatacg    1080
aactatgccg accaaaactc cgttcgctct gactctgccg cttcggacca gaccagcaag    1140
agttacgaca ggggctacag tgataaaaat atagttgccc atagctctgg tagtaggggc    1200
agtcagaatc agaaatcgtc gagttaccgc gctgacaagg acggtttttc ctccagtacg    1260
aatactgaaa aatccaaatt tagttcttcg aatagcgtcg tagaaacttc agatggagct    1320
tctgctagtc gcgaatcatc agcggaggat accaaatcat ccaatagtaa cgttcagagc    1380
gatgaaacag gcgaagaaga ggaattgttc gatgttgtat cttaccagaa aattgaagat    1440
ggcaagcctg taatcataat gaaagttata ccagtcgaga atccgcgtc ccaatcaagt    1500 tcttcgcggt catctcagga gtctgcaagc tatagcagca gcagcagttc atcgacacta    1560
agtgaagact cttccgaggt ggatattgat cttggcaatt taggctggtg gtggaattca    1620
gacaataagg cacaaagagc ggcaggcggc gccacaaagt ctgaagcttc atcatccact    1680
caagctacta cagtcagtgg cgcagacgac agtgctgatt cttacacctg gtggtggaat    1740
cctagacgat caagcagctc ctcttcatca gcaagttcta gcagctctgg ctccaatgtt    1800
ggtggttcct ctcaatccag cggtcagagc acttctggaa gtaatgcccg cggtcatcta    1860
ggaaccgttt cgtccactgg cagtaccagt aacaccgatt caagctcaaa aagtgcagga    1920
tcccgtacat ccggcggtac gagcacttat ggatatagct ccagccatcg tggtggaagc    1980
gtatcatcca ccggcagttc cagcaacact gattcaagca caaagaatgc aggatccagt    2040
acatctggcg gtacgagcac ttatggatat agctctagcc atcgtggtgg aagtgtatca    2100
tccaccggca gttccagcaa cactgattca agcacaaaga gtgcaggatc cagtacatcc    2160
ggcggtacga gcacttacgg atatagctcc aggcatcgtg gtggaagcgt atcatccacc    2220
ggcagttcca gcaacactga ttcaagcaca aagaatgcag gatcccgtac atccggcggt    2280
acgagcactt atggatatag ctccagccat cgtggtggaa gcgtatcatc caccggcagt    2340
tccagcaaca ctgattcaag cacaaagaat gcaggatccc gtacatccgg cggtacgagc    2400
acttatggat atagctccag ccatcgtggt ggaagcgtat catccaccgg cagttccagc    2460
aacactgatt caagcacaaa gaatgcagga tcccgtacat ccggcggtac gagcacttat    2520
ggatatagct ccagccatcg tggtggaagc gtatcatcca ccggcagttc cagcaacact    2580
gattcaagca caaagaatgc aggatccagt acatccggcg gtagcagcac ttatggatac    2640
agttccgaca gtcgtgatgg aagtgtatca tccaccggca gttccagtaa cactgatgca    2700
agcacagacc tggcaggatc cagtacatcc ggcggtagca gcacttatgg atacagttcc    2760
gacagtcgtg atggaagtgt atcatccacc ggcagttcca gtaacactga tgcaagcaca    2820
gacctggcag gatccagtac atccggcggt agcagcactt atggatacag ttccgacagt    2880
cgtgatggaa gtgtatcatc caccggcagt tccagtaaca ctgatgcaag cacagacctt    2940
acaggatcca gtacatccgg cggtagcagc acttatggat acagttccga cagtcgtgat    3000
ggaagtgtat catccaccgg cagttccagt aacactgatg caagcacaga cctggcagga    3060
tccagtacat ccggcggtag cagcacttat ggatatagct caagcaatcg tgatggaagt    3120
gtatcggcca ctggcagttc cagtaacact gatgcaagca ccacagaaga atccaccacg    3180
tccgctggta gcagcactga aggatatagt tccagtagcc atgatggaag cgtaacatcc    3240
accgacggtt ccagcacaag tggaggagct tcttccagct cagcgtcaac cgccaaaagc    3300
gacgccgcgt catctgaaga cggtttctgg tggtggaata aaggaaatc aggatccggt    3360 cacaaaagcg ctaccgtaca gtcatccaca accgataaga cgagcaccga cagtgccagc    3420
```

```
agcaccgatt ccacctcaag cacgtccggg gcaagcacaa ccacttcagg cagttcttct    3480
acctcgggcg gttcaagtac atcggacgct cctccactt cgtctagtgt ttccaggagt    3540
catcattcag gcgtgaacag acttttacac aagcctggtc aaggaaaaat atgcctttgc   3600
ttcaaaaaca tattcgatat tccttaccat ctccgtaaga atatcggtgt t             3651

<210> SEQ ID NO 4
<211> LENGTH: 76
<212> TYPE: PRT
<213> ORGANISM: Artificial Sequence
<220> FEATURE:
<223> OTHER INFORMATION: Peptides derived from sericin

<400> SEQUENCE: 4

Ser Ser Thr Gly Ser Ser Ser Asn Thr Asp Ser Asn Ser Asn Ser Ala
1               5                   10                  15

Gly Ser Ser Thr Ser Gly Gly Ser Ser Thr Tyr Gly Tyr Ser Ser Asn
                20                  25                  30

Ser Arg Asp Gly Ser Val Ser Ser Thr Gly Ser Ser Ser Asn Thr Asp
            35                  40                  45

Ser Asn Ser Asn Ser Ala Gly Ser Ser Thr Ser Gly Gly Ser Ser Thr
        50                  55                  60

Tyr Gly Tyr Ser Ser Asn Ser Arg Asp Gly Ser Val
65                  70                  75

<210> SEQ ID NO 5
<211> LENGTH: 4
<212> TYPE: PRT
<213> ORGANISM: Artificial Sequence
<220> FEATURE:
<223> OTHER INFORMATION: Recognition site for factor Xa

<400> SEQUENCE: 5

Ile Glu Gly Arg
1

<210> SEQ ID NO 6
<211> LENGTH: 61
<212> TYPE: DNA
<213> ORGANISM: Artificial Sequence
<220> FEATURE:
<223> OTHER INFORMATION: DNA fragment coded a part of the peptide
      derived from sericin

<400> SEQUENCE: 6
gtgatcaatc gaaggtcgct cgagtactgg ttcttcttct aacaccgact ctaactctaa    60
c                                                                    61

<210> SEQ ID NO 7
<211> LENGTH: 69
<212> TYPE: DNA
<213> ORGANISM: Artificial Sequence
<220> FEATURE:
<223> OTHER INFORMATION: DNA fragment coded a part of the peptide
      derived from sericin

<400> SEQUENCE: 7
tctgctggtt cttctacctc tggtggttct tctacctacg gttactcttc taactctcgt    60
gacggttct                                                            69

<210> SEQ ID NO 8
```

```
<211> LENGTH: 65
<212> TYPE: DNA
<213> ORGANISM: Artificial Sequence
<220> FEATURE:
<223> OTHER INFORMATION: DNA fragment coded a part of the peptide
      derived from sericin

<400> SEQUENCE: 8
gtttcttcta ccggttcttc ttctaacacc gactctaact ctaactctgc tggttcttct    60
acctc                                                                65

<210> SEQ ID NO 9
<211> LENGTH: 65
<212> TYPE: DNA
<213> ORGANISM: Artificial Sequence
<220> FEATURE:
<223> OTHER INFORMATION: DNA fragment coded a part of the peptide
      derived from sericin

<400> SEQUENCE: 9
tggtggttct tctacctacg gttactcttc taactctcgt gacggatccg tttaatagct    60
gagcg                                                                65

<210> SEQ ID NO 10
<211> LENGTH: 69
<212> TYPE: DNA
<213> ORGANISM: Artificial Sequence
<220> FEATURE:
<223> OTHER INFORMATION: DNA fragment coded a part of the peptide
      derived from sericin

<400> SEQUENCE: 10
cagagttaga gttagagtcg gtgttagaag aagaaccagt actcgagcga ccttcgattg    60
atcactgca                                                            69

<210> SEQ ID NO 11
<211> LENGTH: 69
<212> TYPE: DNA
<213> ORGANISM: Artificial Sequence
<220> FEATURE:
<223> OTHER INFORMATION: DNA fragment coded a part of the peptide
      derived from sericin

<400> SEQUENCE: 11
aaacagaacc gtcacgagag ttagaagagt aaccgtaggt agaagaacca ccagaggtag    60
aagaaccag                                                            69

<210> SEQ ID NO 12
<211> LENGTH: 65
<212> TYPE: DNA
<213> ORGANISM: Artificial Sequence
<220> FEATURE:
<223> OTHER INFORMATION: DNA fragment coded a part of the peptide
      derived from sericin

<400> SEQUENCE: 12
accagaggta gaagaaccag cagagttaga gttagagtcg gtgttagaag aagaaccggt    60
agaag                                                                65

<210> SEQ ID NO 13
<211> LENGTH: 65
<212> TYPE: DNA
<213> ORGANISM: Artificial Sequence
<220> FEATURE:
```

```
-continued

<223> OTHER INFORMATION: DNA fragment coded a part of the peptide
      derived from sericin

<400> SEQUENCE: 13
aattcgctca gctattaaac ggatccgtca cgagagttag aagagtaacc gtaggtagaa    60
gaacc                                                               65
```